United States Patent
Maier

(10) Patent No.: US 8,554,306 B2
(45) Date of Patent: Oct. 8, 2013

(54) GUIDE WIRE NAVIGATION

(75) Inventor: Christian Maier, Munich (DE)

(73) Assignee: Brainlab AG, Feldkirchen (DE)

( * ) Notice: Subject to any disclaimer, the term of this patent is extended or adjusted under 35 U.S.C. 154(b) by 2184 days.

(21) Appl. No.: 11/385,251

(22) Filed: Mar. 21, 2006

(65) Prior Publication Data

US 2006/0241420 A1 Oct. 26, 2006

Related U.S. Application Data

(60) Provisional application No. 60/671,786, filed on Apr. 15, 2005.

(30) Foreign Application Priority Data

Mar. 22, 2005 (EP) .................................... 05006219

(51) Int. Cl.
*A61B 5/06* (2006.01)
(52) U.S. Cl.
USPC ............................................ 600/424; 606/96
(58) Field of Classification Search
None
See application file for complete search history.

(56) References Cited

U.S. PATENT DOCUMENTS

| | | | | |
|---|---|---|---|---|
| 5,274,551 A | * | 12/1993 | Corby, Jr. ........................ | 600/433 |
| 2003/0229279 A1 | * | 12/2003 | Amstutz et al. ................ | 600/424 |
| 2004/0015075 A1 | * | 1/2004 | Kimchy et al. ................ | 600/424 |
| 2006/0030771 A1 | * | 2/2006 | Levine et al. .................. | 600/424 |
| 2006/0173291 A1 | * | 8/2006 | Glossop .......................... | 600/424 |
| 2006/0189864 A1 | * | 8/2006 | Paradis et al. ................. | 600/407 |

FOREIGN PATENT DOCUMENTS

| DE | 101 18 570 A1 | 7/2002 |
|---|---|---|
| EP | 1 413 257 A1 | 4/2004 |
| WO | 03/043485 A2 | 5/2003 |

OTHER PUBLICATIONS

Dynamics of Transversely Vibrating Beams Using Four Engineering Theories Han, Seon M.; Benaroya, Haym; Wei, Timothy Journal of Sound and Vibration, vol. 225, pp. 935-988 (1999).*

* cited by examiner

*Primary Examiner* — Long V. Le
*Assistant Examiner* — Bradley Impink
(74) *Attorney, Agent, or Firm* — Renner, Otto, Boisselle & Sklar, LLP

(57) ABSTRACT

A system and method for identifying the position of the distal end of a bone guide wire is provided. A position and orientation of the proximal end of the guide wire is identified with the aid of a medical, optical tracking and navigation system and a reference device on the proximal end of the guide wire. The orientation of a bone in which the distal end of the guide wire is located is identified with the aid of the medical, optical tracking and navigation system and a reference device on the bone. By means of the ancillary conditions for the course of the guide wire, which are given by the position and orientation of the proximal end and the orientation of the bone, and by taking into account the physical properties of the guide wire, the position of the distal end of the bone guide wire is identified with the assistance of a computer.

15 Claims, 2 Drawing Sheets

GUIDE WIRE NAVIGATION

RELATED APPLICATION DATA

This application claims priority of U.S. Provisional Application No. 60/671,786 filed on Apr. 15, 2005, which is incorporated herein by reference in its entirety.

FIELD OF THE INVENTION

The present invention relates to guide wires and, more particularly, to a system and method for navigating a guide wire.

BACKGROUND OF THE INVENTION

Guide wires typically are used, for example, to "thread" bone fragments after a bone fracture and before introduction of an intramedullary pin. The guide wire can be a long, flexible and relatively thin rod with a proximal end at which the guide wire can be gripped and with a distal end that can be advanced through the bone channel or the channels of bone fragments, in order to thread the fragments.

In this activity, it would be advantageous if the location of the distal end of the guide wire were known at any time. It would then be possible to ascertain whether said distal end has been advanced far enough to guarantee sufficient threading.

At present, the proximal end or the whole guide wire is tracked in a tubular bone with the aid of fluoroscopic recordings (e.g., x-ray recordings or the like), wherein the position of the guide wire is visualised using C-arc x-ray equipment and, thus, the position of the distal end can be compared to the bone or bone fragments. The relatively high number of single x-ray recordings or even continuous x-ray recordings needed for this subjects both the patient and the surgeon to high radiation loads.

In medical technology, the use of magnetic field navigation has been proposed for the targeted insertion of cannulae or catheters. Examples of magnetic field navigation are shown in U.S. Pat. Nos. 6,104,944 and 6,783,536 B2. However, magnetic field navigation or similarly functioning types of navigation that navigate or positionally detect hidden instruments inside a body are technically complex and susceptible to faults.

Optical navigation systems are known, for example, from DE 196 39 615 A1, which is incorporated herein by reference in its entirety. However, up until now it has not been deemed possible to positionally determine an instrument section of a flexible instrument lying inside a patient's body by means of an optical navigation and tracking system. This is simply due to the fact that the course of the flexible instrument has not been deemed to be detectable and it has not been possible to expediently arrange an optical reference array on the flexible part or on the tip of the flexible part, since this part is located inside the body structures.

SUMMARY OF THE INVENTION

The present invention enables the distal end of a guide wire, such as a bone guide wire, to be identified within an object, such as a bone, without the patient and the surgeon being exposed to high doses of radiation and without the need for large scale equipment, such as magnetic navigation and tracking systems, for example. Furthermore, the present invention enables positions of the guide wire to be simply identified using available and/or existing means, while minimizing potential faults.

The invention thus provides a method for identifying the position of the distal end of a bone guide wire, wherein the position and orientation of the proximal end of the guide wire can be identified with the aid of a medical optical tracking and navigation system and a reference device on the proximal end of the guide wire. The orientation of the bone can be identified with the aid of an optical tracking and navigation system (e.g., a medical navigation system) and a reference device on the bone in which the distal end of the guide wire is located. By means of the ancillary conditions for the course of the guide wire, which can be determined by the position and orientation of the proximal end and the orientation of the bone, and by taking into account the physical properties of the guide wire, the position of the distal end of the bone guide wire can be identified with computer assistance. In the method, positions can be identified with the assistance of the computer of the tracking and navigation system.

An image support method for using a bone guide wire can identify the position of the distal end of the bone guide wire in accordance with the method described above. In addition, this position can be provided on an image output of the tracking and navigation system, in relation to the bone arrangement.

The invention further provides a device for identifying the position of the distal end of the bone guide wire, and can comprise a medical optical tracking and navigation system, a reference device on the proximal end of the guide wire and a reference device on the bone in which the distal end of the guide wire is located. The device also can include a computer, which by means of the ancillary conditions for the course of the guide wire (which can be determined by the position and orientation of the proximal end and the orientation of the bone), and by taking into account the physical properties of the guide wire, can identify the position of the distal end of the bone guide wire.

The computer can be the computer of the tracking and navigation system, which can comprise an image output that provides the identified position of the distal end in relation to the bone arrangement.

The forgoing and other features and embodiments of the invention are hereinafter discussed with reference to the drawings.

BRIEF DESCRIPTION OF THE DRAWINGS

The forgoing and other embodiments of the invention are hereinafter discussed with reference to the drawings.

DETAILED DESCRIPTION

Figure 1:
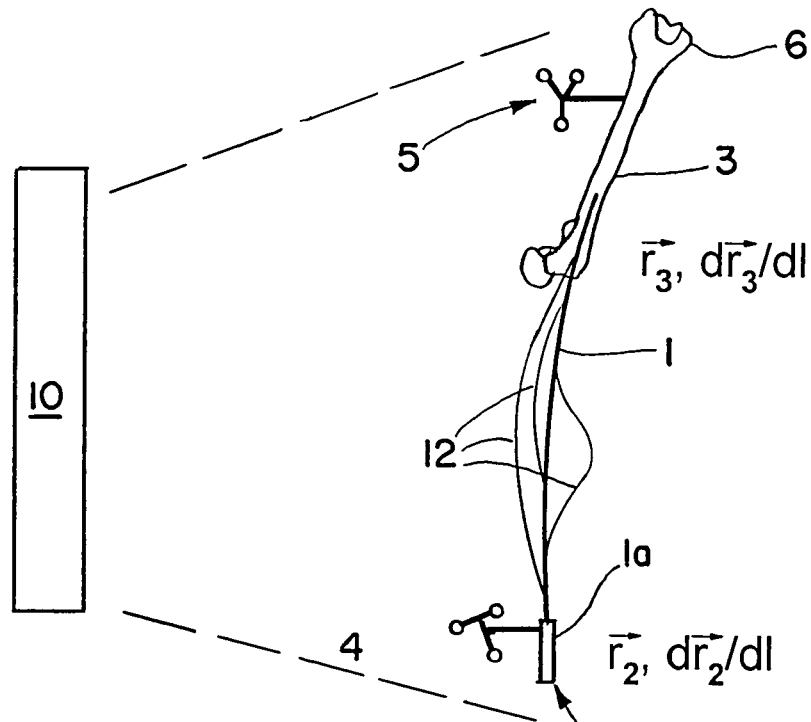
FIG. 1 is a schematic diagram showing an exemplary mapping of the surroundings of a guide wire navigated in accordance with the invention.

Referring to FIG. 1, there is shown a guide wire 1 that includes a grip 1a at its proximal end 2. A first navigation reference device 4 is attached to the grip 1a of the guide wire 1, and a second navigation reference device 5 is arranged on a bone 6. The navigation reference devices 4 and 5 can be positionally detected by a navigation and tracking system 10, which is only represented schematically. Although not shown, the navigation and tracking system 10 can include tracking cameras, a data processing facility and an image output and data input means, for example, or any other component/system used in navigation and tracking systems. The system 10 can be a conventional optical navigation and tracking system, for example, and the reference devices 4 and 5 can be formed as reference stars that reflect (passive) or emit (active) invisible (e.g., infrared) light. The navigation system 10 can be one such as is described as a "Neuro-navigation System" in DE 196 39 615 A1, for example.

The navigation and tracking system 10 can identify the position and orientation of the proximal end 2 ($r_2$, $dr_2/dl$) of the guide wire 1. The position and orientation of the bone 6 also can be identified and, in particular, the orientation of the inner tubular channel (not shown) in the bone 6. What is sought is the vector $r_3$ (i.e., the position of the distal end 3 of the guide wire 1).

Using the steps described herein, the insertion depth of the distal end 3 can be identified under certain conditions. To this end, and contrary to all previous approaches, optical navigation, as opposed to magnetic navigation, is used. The grip 1a of the guide wire 1 (distal end 2) can be easily tracked and, because the bone orientation is already known via reference device 5, the orientation of the axis of the tubular bone into which the guide wire 1 is inserted is known. This allows the insertion depth of the guide wire 1 to be virtually displayed on a computer monitor.

The invention takes into account the high degree of bending of the flexible guide wire 1. This is possible because the orientation of the guide wire 1 in the area of the tip is known. This knowledge can be used to take into account the bending, which otherwise would not be detectable. Many contours are theoretically possible and some are shown in FIG. 1 with the reference indicator 12. Up until now, optical navigation systems have only been used to track and represent rigid bodies for which the position and orientation at a single point determines the position and orientation of the whole structure. The invention described herein allows the tip or distal end 3 of a flexible guide wire 1 to be tracked, without having to use invasive imaging methods (e.g., x-ray C-arc).

It is noted that the present invention enables the position of the distal end of any flexible elongated instrument to be identified, provided the conditions described herein are observed. In particular, the orientation in the area of the distal end 3 should be known (in the present example, any channel for which the orientation is known is available), since the proximal end 2 can be optically tracked (in its position and orientation) and since the flexible instrument exhibits certain physical properties that are explained in more detail below.

The navigation system 10 thus tracks and shows the insertion depth for a flexible medical or surgical wire in a tubular bone. Although not represented separately in FIG. 1, the navigation system 10 includes a camera system that tracks the position of the reference marker array 4 attached to the grip 1a of the guide wire 1 and the position of the reference marker array 5 arranged on the tubular bone 6. The navigation software can be configured so as to assign the three-dimensional position and orientation of an axis to the three-dimensional position and orientation of the reference marker arrays 4 and 5. Using this information, boundary or ancillary conditions for the shape of the guide wire can be defined, such that it is possible to ascertain the depth of penetration of the guide wire 1 into the bone 6. The same naturally applies to larger bone fragments that can occur after a fracture, provided the fragments (or one of the fragments) are fitted with tracking devices, such as reference marker arrays, for example.

In order to track and represent the penetration depth of a flexible bone guide wire 1, the following conditions should be fulfilled:

a) the bone guide wire, expressed in terms of elasticity theory, can be regarded as a stiff or rigid rod. "Stiff" means that the persistency length of the wire ($L_p$) is much larger than the length of the wire (L). The persistency length is defined as the distance between two points on the contour of the wire for which the auto-correlation function of the tangent angle of the contour to the 1/eth part declines (e=Eulerian number). It is known from polymer theory that the persistency length can be written as:

$L_p = YI/k_B \cdot T$ (Y=Young modulus, I=geometrical moment of inertia of the wire cross-section, $k_B$=Boltzmann's constant; T=temperature). Using typical values for Y, I and T, a simple calculation shows that $L_p \gg L$.

b) The length of the wire is constant. Since the Young modulus for the material of the guide wire is approximately 100 GPa, it can be shown that the forces occurring only lead to relative changes in length of 0.001 mm and less.

In one type of calculation, the contour of the wire can be described as a third-order vectorial differential equation. In order to solve this equation, three vectorial ancillary conditions must be known, these being:

1. the position of the proximal wire end 2 (on the grip);
2. the orientation of the proximal wire end; and
3. the orientation of a point on the wire close to the distal wire end.

Figure 2:
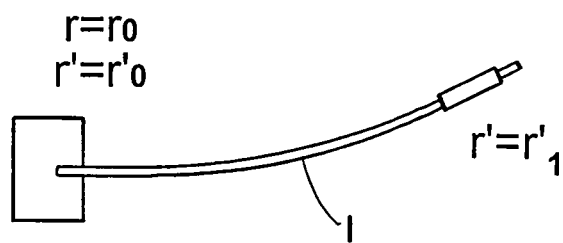
FIG. 2 is a schematic representation of the guide wire for the purpose of theoretical discussion.

From 1) to 3), the ancillary conditions can be defined and the differential equation solved using numerical methods. Together with the conditions a) and b), relevant information on the penetration depth of the wire 1 can be extracted and displayed on the image display of the navigation system 10. Figuratively speaking, the knowledge of the orientation of the guide wire 1 at a position in the vicinity of its inserted end (distal end 3) allows the correct contour to be found from the multitude of possible contours (exemplary possible contours are those shown in FIG. 1 with the reference sign 12, the distal point of which lies in the bone 6, but which as a whole take a different course). A somewhat more detailed description of the fundamentals of elasticity theory is given in the following, wherein Equations 1.9 and 1.10 refer to FIG. 2.

The complete system of equilibrium conditions for a rod bent in any way is given by Equation 1.1 and 1.2:

$$\frac{dF}{dl} = -K \quad \text{(Eq. 1.1)}$$

$$\frac{dM}{dl} = F \times t \quad \text{(Eq. 1.2)}$$

wherein F denotes the inner tension forces, K being the external force acting on the rod, M is the torque of the inner tensions acting on the cross-sectional area, t is the unit vector of the tangents to the rod, I is the arching length on the rod, and x denotes the product of the vectors.

The x component of Equation 1.2 is $$\frac{dM_x}{dl} = F_y t_z - F_z t_y \quad \text{(Eq. 1.3)}$$

If this equation is differentiated twice according to the variable l, two further equations are obtained, with the aid of which $F_y$ and $F_z$ can be eliminated. In addition, the differentials $dF_y/dl$ and $dF_z/dl$ can be expressed by means of Equation 1.1 by the components of the external force. Thus, the following is obtained for $M_x$:

$$M_x''' = \left(M_x'' - \frac{t_z'}{t_z}M_x' + K_y t_z - K_z t_y\right)\left(\frac{t_y t_z'' - t_y'' t_z}{t_y t_z' - t_y' t_z}\right) + \frac{t_z''}{t_z}M_x' - K_y' t_x - 2K_y t_x' + K_z' t_y + 2K_z t_y'$$ (Eq. 1.4)

Analogous equations follow for $M_y$ and $M_z$, if the substitution $x \to y$, $y \to z$, $z \to x$ is made once or twice, respectively.

If the external forces only act on single isolated points, then K=0 in the rod sections between the impact points of the external forces, and Equation 1.4 is thus simplified to:

$$M_x''' = \left(M_x'' - \frac{t_z'}{t_z}M_x'\right)\left(\frac{t_y t_z'' - t_y'' t_z}{t_y t_z' - t_y' t_z}\right) + \frac{t_z''}{t_z}M_x'$$ (Eq. 1.5)

If it is assumed that the cross-section of the rod is circular, then the torque can be written as:

$$M = EIt \times \frac{dt}{dl}$$ (Eq. 1.6)

with E as the elasticity modulus of the rod material, I as the geometrical moment of inertia of the rod cross-section ($I=\pi R^4$ for a circular cross-section having a radius R).

Inserting the x component from Equation 1.6 into Equation 1.5 gives a differential equation of the form:

$$f_1\left(\frac{d^4 t_y}{dl^4}, \frac{d^4 t_z}{dl^4}, \frac{d^3 t_y}{dl^3}, \frac{d^3 t_z}{dl^3}, \frac{d^2 t_y}{dl^2}, \frac{d^2 t_z}{dl^2}, \frac{dt_y}{dl}, \frac{dt_z}{dl}, t_y, t_z\right) = 0$$ (Eq. 1.7)

with $$t = \frac{dr}{dl}$$

(r=radius vector from the coordinates of the origin to any point on the rod), Equation 1.7 gives a differential equation of the form:

$$g_1\left(\frac{d^5 y}{dl^5}, \frac{d^5 z}{dl^5}, \frac{d^4 y}{dl^4}, \frac{d^4 z}{dl^4}, \frac{d^3 y}{dl^3}, \frac{d^3 z}{dl^3}, \frac{d^2 y}{dl^2}, \frac{d^2 z}{dl^2}, \frac{dy}{dl}, \frac{dz}{dl}\right) = 0$$ (Eq. 1.8)

Alongside $g_1$, there are also two further differential equations ($g_2$ and $g_3$) which arise from the aforementioned index substitution. A coupled differential equation system has been abstracted in which the variable I and the functions x(I), y(I) and z(I) do not explicitly appear. As a result, the order of the differential equations is reduced by two, to a third-order coupled differential equation system or third-order vectorial differential equation. Solving requires three vectorial ancillary conditions.

Ancillary Conditions:

The rod is clamped on one side, then the following applies:

$$r(l=0) = r_0$$ (Eq. 1.9)

$$\left.\frac{dr}{dl}\right|_{(l=0)} = r_0'$$

The rod moves at a location in the space ($r=r_1$) parallel to a "tube", i.e., at this point, its direction is predetermined. The point on the rod for which this condition applies is not known, however this ancillary condition $$\left.\frac{dr}{dl}\right|_{(r=r_1)} = r_1'$$ (Eq. 1.10)

can be fulfilled, if, from the multitude of possible solutions which satisfy Equation 1.9, the solution which fulfils Equation 1.10 is selected.

Figure 3:
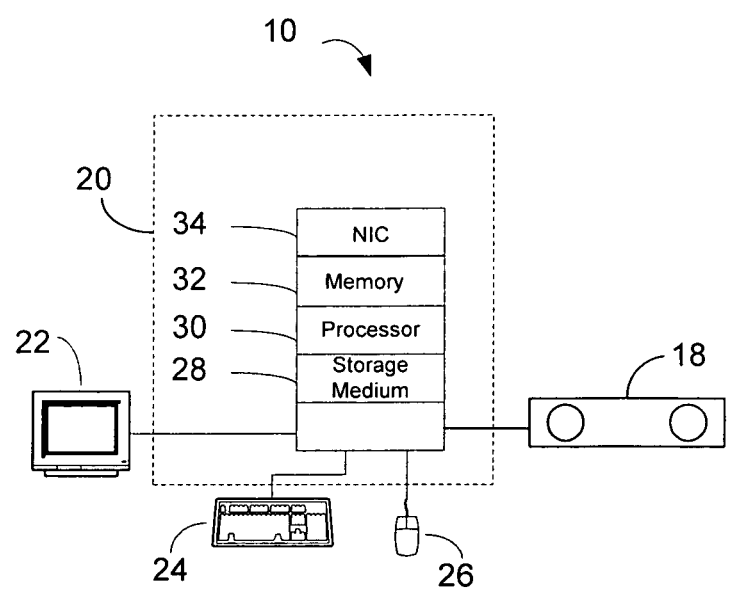
FIG. 3 is a block diagram of an exemplary computer system that can be used to implement the method of the present invention.

Moving to FIG. 3, an exemplary computer or navigation system 10 for executing a computer program in accordance with the present invention is illustrated. The navigation system 10 can be communicatively coupled to the cameras 18 to receive positional data therefrom, and to display three-dimensional positional data. The navigation system 10 includes a computational unit 20 for processing data, and a display 22, such as a CRT, LCD, or the like, for viewing system information. A keyboard 24 and pointing device 26 may be used for data entry, data display, screen navigation, etc. The keyboard 24 and pointing device 26 may be separate from the computational unit 20 or they may be integral to it. A computer mouse or other device that points to or otherwise identifies a location, action, etc., e.g., by a point and click method or some other method, are examples of a pointing device. Alternatively, a touch screen (not shown) may be used in place of the keyboard 24 and pointing device 26. A touch screen is well known by those skilled in the art and will not be described in herein.

Included in the computational unit 20 is a storage medium 28 for storing information, such as application data, screen information, programs, etc. The storage medium 28 may be a hard drive, for example. A processor 30, such as an AMD Athlon 64™ processor or an Intel Pentium IV® processor, combined with a memory 32 and the storage medium 28 execute programs to perform various functions, such as data entry, numerical calculations, screen display, system setup, etc. A network interface card (NIC) 34 allows the computational unit 20 to communicate with devices external to the navigation system 10.

The actual code for performing the functions described herein can be readily programmed by a person having ordinary skill in the art of computer programming in any of a number of conventional programming languages based on the disclosure herein. Consequently, further detail as to the particular code itself has been omitted for sake of brevity.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for identifying the position of a distal end of a guide wire inserted within an object having a channel, wherein a first trackable reference device is associated with a proximal end of the guide wire, and a second trackable reference device is associated with the object, comprising:
   identifying a position and orientation of the proximal end of the guide wire via the first reference device;
   identifying an orientation of the channel in which the distal end of the guide wire is located via the second reference device; and
   identifying, with computer assistance, the position of the distal end based on at least one physical property of the guide wire and ancillary conditions for the course of the guide wire, wherein the ancillary conditions are given by the position and orientation of the proximal end and the orientation of the channel in the object.

2. The method according to claim 1, wherein the step of identifying includes using an optical tracking and navigation system to perform the identification.

3. The method according to claim 2, wherein the step of using computer assistance includes using a computer of the tracking and navigation system.

4. The method according to claim 2, wherein the object is a bone, further comprising displaying the position of the distal end in relation to the bone arrangement on an image output device of the tracking and navigation system.

5. The method according to claim 1, wherein the object is a bone.

6. A system for identifying a position of a distal end of a guide wire within an object having a channel, comprising:
   an optical tracking and navigation system;
   a first reference device associated with a proximal end of the guide wire for determining a position and orientation of the proximal end;
   a second reference device associated with the object in which the distal end of the guide wire is located for determining an orientation of the object and the channel; and
   a computer configured to identify the position of the distal end of the guide wire, wherein the position is based on at least one physical property of the guide wire and ancillary conditions for the course of the guide wire, said ancillary conditions given by the position and orientation of the proximal end and the orientation of the channel in the object.

7. The system according to claim 6, wherein the computer is a computer of the tracking and navigation system.

8. The device according to claim 6, wherein the tracking and navigation system comprises an image output device that displays the identified position of the distal end in relation to the bone arrangement.

9. A computer program product, comprising a computer useable medium having a computer readable program code embodied therein, said computer readable program code adapted to be executed to implement the method in accordance with claim 1.

10. A program embodied in a computer-readable medium for identifying the position of a distal end of a guide wire inserted within an object, wherein a first trackable reference device is associated with a proximal end of the guide wire, and a second trackable reference device is associated with the object having a channel, comprising:
   code that identifies a position and orientation of the proximal end of the guide wire via the first reference device;
   code that identifies an orientation of the channel based on an orientation of the object in which the distal end of the guide wire is located via the second reference device; and
   code that identifies the position of the distal end based on at least one physical property of the guide wire and ancillary conditions for the course of the guide wire, wherein the ancillary conditions are given by the position and orientation of the proximal end and the orientation of the channel in the object.

11. The method according to claim 1, wherein the object is a bone, further comprising displaying the position of the distal end in relation to the bone arrangement on an image output device of the tracking and navigation system.

12. The method according to claim 1, wherein identifying, with computer assistance, the position of the distal end based on at least one physical property of the guide wire and ancillary conditions for the course of the guide wire, comprises:
   describing a contour of the guide wire as a third-order vectorial differential equation; and
   solving the differential equation.

13. The method according to claim 12, wherein solving the differential equation includes using the position and orientation of the proximal end of the guide wire, and an orientation of a point on the guide wire closest to the guide wire distal end to solve the differential equation.

14. The method according to claim 1, wherein identifying the position and orientation of the proximal end of the guide wire and the orientation of the channel includes optically identifying the position and orientation of the proximal end and the orientation of the channel.

15. The program according to claim 10, wherein the code that identifies a position and orientation of the proximal end and the code that identifies the orientation of the channel includes code configured for optical identification of the position and orientation of the proximal end and of the orientation of the channel.

* * * * *